United States Patent [19]
Cohen

[11] Patent Number: 5,509,934
[45] Date of Patent: Apr. 23, 1996

[54] PROSTHETIC KNEE TIBIAL COMPONENT CONSTRUCTED OF SYNTHETIC POLYMERIC MATERIAL

[75] Inventor: Robert C. Cohen, Rockaway Township, N.J.

[73] Assignee: Osteonics Corp., Allendale, N.J.

[21] Appl. No.: 351,552

[22] Filed: Dec. 7, 1994

Related U.S. Application Data

[63] Continuation of Ser. No. 145,295, Oct. 29, 1993, abandoned, which is a continuation of Ser. No. 946,011, Sep. 15, 1992, abandoned, which is a continuation of Ser. No. 843,648, Feb. 28, 1992, abandoned.

[51] Int. Cl.$^6$ .................................................. A61F 2/38
[52] U.S. Cl. ........................................................ 623/20
[58] Field of Search ................................. 623/16, 18, 20

[56] References Cited

U.S. PATENT DOCUMENTS

| | | | |
|---|---|---|---|
| 3,728,742 | 4/1973 | Averill et al. | 623/20 |
| 3,816,855 | 6/1974 | Saleh | 623/20 |
| 3,869,731 | 3/1975 | Waugh et al. | 623/20 |
| 4,024,588 | 5/1977 | Janssen et al. | |
| 4,081,866 | 4/1978 | Upshaw et al. | 623/20 |
| 4,134,158 | 1/1979 | Laure. | |
| 4,209,861 | 7/1980 | Walker et al. | |
| 4,216,549 | 8/1980 | Hillberry et al. | |
| 4,257,129 | 3/1981 | Volz. | |
| 4,822,362 | 4/1989 | Walker et al. | |
| 4,963,153 | 10/1990 | Noesberger | 623/20 |
| 4,986,833 | 1/1991 | Worland | 623/19 |
| 5,019,104 | 5/1991 | Whiteside et al. | 623/20 |
| 5,021,061 | 6/1991 | Wevers et al. | 623/20 |
| 5,137,536 | 8/1992 | Koshino | 623/20 |

OTHER PUBLICATIONS

"Effects of Tibial Components on Load Transfer in the Upper Tibia", Department of Orthopaedic Surgery, Brigham and Women's Hospital, 1982.
"Symposium: Total Knee Replacement", Contemporary Orthopaedics, pp. 101–122, Mar. 1983.
"Replacement of the Knee", Springer–Verlag, 1984.
"Total–Condylar Knee Arthroplasty", Springer–Verlag, 1985.
"The Effect of Conformity, Thickness, and Material on Stresses in Ultra–High Molecular Weight Components for Total Joint Replacement", *The Journal of Bone & Joint Surgery*, 1986.
"Orthopaedic Biometerials in Research and Practice" Livingstone 1988.
"Controversies of Total Knee Arthroplasty" pp. 70–72, Rover Press 1991.

*Primary Examiner*—Mary Beth Jones
*Attorney, Agent, or Firm*—Samuelson & Jacob

[57] ABSTRACT

A tibial component for use in a prosthetic knee implant is constructed of a one-piece unitary member of synthetic polymeric material including a bearing portion having bearing surfaces for accepting the load imposed by the femoral component of the prosthetic knee implant and a keel projecting axially downwardly from the bearing portion and having flanges extending from a generally centrally located post outwardly at an angle to one another to be placed beneath the bearing surfaces of the bearing portion for reinforcing the bearing portion against the load imposed by the femoral component during service, while providing strength as well as rigidity and added stability for providing a relatively inexpensive alternative to metallic tibial components in recipients where the levels of performance offered by the higher cost metallic tibial components are not required.

14 Claims, 3 Drawing Sheets

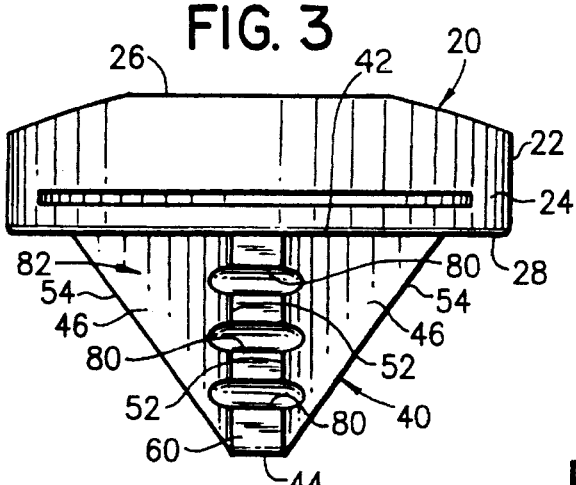
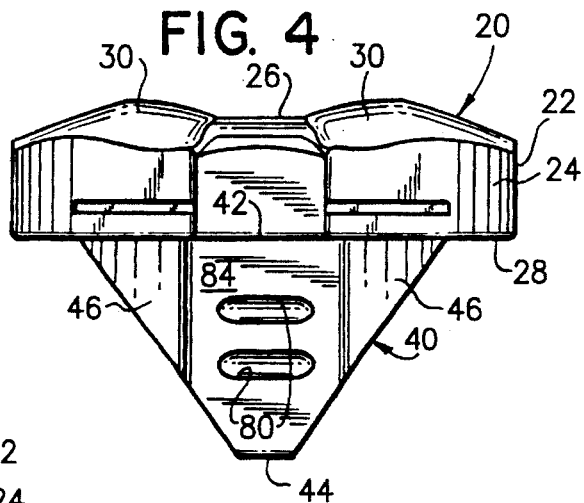
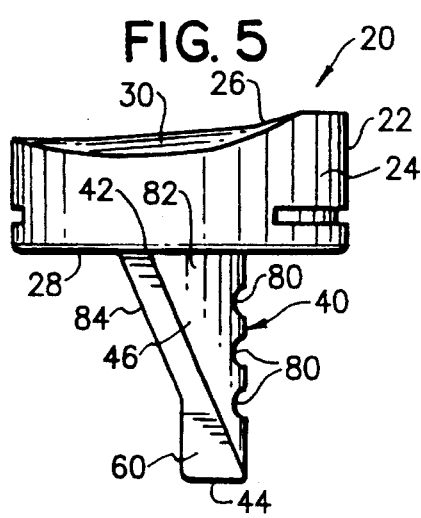
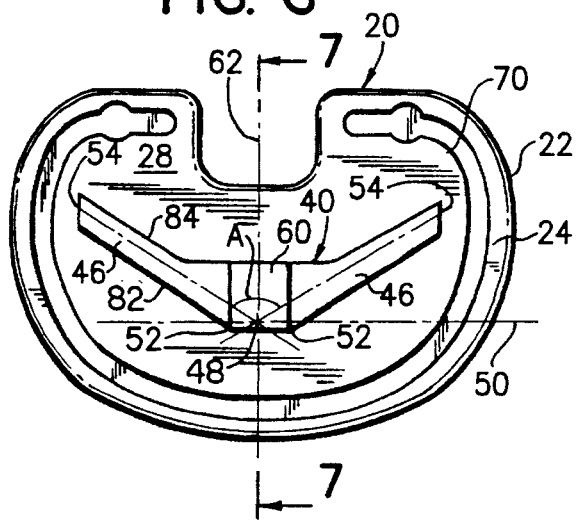

PROSTHETIC KNEE TIBIAL COMPONENT CONSTRUCTED OF SYNTHETIC POLYMERIC MATERIAL

This application is a continuation, of application Ser. No. 08/145,295,filed Oct. 29, 1993, now abandoned which is a continuation of application Ser. No. 07/946,011, filed Sep. 15, 1992,now abandoned which is a continuation of application Ser. No. 07/843,648, filed Feb. 28, 1992, abandoned.

The present invention relates generally to prosthetic implant devices used for replacing natural joints in the body and pertains, more specifically, to a tibial component used in a knee prosthesis.

A wide variety of knee protheses now is available for the replacement of the natural knee joint. For the most part, these knee prostheses are constructed of multiple component parts, many of which are made of metal alloys selected for strength and durability, as well as for compatibility with the biological materials at the site of the implanted prosthesis. In most of the accepted arrangements, a bearing member constructed of a synthetic polymeric material, such as high-density polyethylene, is interposed between the condylar elements of a metallic femoral component and a tibial tray which is a part of the complementary tibial component of the prosthesis.

It has been suggested that under certain circumstances a unitary tibial component constructed essentially entirely of a synthetic polymeric material could replace the multiple component parts of the tibial component, thereby reducing the complexity of the prosthetic knee, as well as simplifying the implant procedure. Although not necessarily as durable over the long term as a metallic tibial component, a unitary tibial component constructed of a synthetic polymeric material would be considerably less expensive. Thus, where longevity is not a primary factor, a less expensive alternative to the metallic tibial component would be advantageous.

Accordingly, the present invention provides a tibial component constructed in one piece of a synthetic polymeric material and having a structure which enables exemplary performance for an adequate service life, thereby offering a more practical alternative, where indicated as acceptable, to the more complex and more expensive metallic tibial components currently available. As such, the present invention attains several objects and advantages, some of which are summarized as follows: Enables the construction of a tibial component in a one-piece unitary structure of a synthetic polymeric material, which tibial component provides adequate performance for certain recipients at reduced expense; provides a relatively inexpensive alternative to more costly tibial components constructed of metallic parts where it is indicated that the performance characteristics of the synthetic polymeric tibial component are adequate for a particular recipient; provides a unitary synthetic polymeric tibial component having a structural configuration which reinforces the tibial component against loads imposed during use so as to enable satisfactory performance over an adequate service life; employs a structural configuration which enables increased stability for exemplary performance over a wide variety of conditions encountered during service; facilitates the implant of a knee prosthesis employing the tibial component; enables the economical manufacture of a unitary synthetic polymeric tibial component in practical numbers of uniformly high quality.

The above objects and advantages, as well as further objects and advantages, are attained by the present invention which may be described briefly as a tibial component constructed of a one-piece member of synthetic polymeric material for use in a prosthetic knee implant including a femoral component having condylar elements, the tibial component including a bearing portion having an upper surface for confronting the femoral component and a lower surface for engaging the proximal tibia, the tibial component comprising: condylar bearing surface portions along the upper surface of the bearing portion for engaging the condylar elements of the femoral component and accepting the load imposed by the condylar elements of the femoral component during service; and a keel projecting in an axial direction downwardly from a proximal end at the lower surface of the bearing portion to a distal end spaced away from the lower surface, the keel including a pair of flanges extending in the axial direction and establishing a generally V-shaped overall cross-sectional configuration in planes transverse to the axial direction, the V-shaped cross-sectional configuration having an apex located essentially centrally of the bearing portion along the medial-lateral direction; the flanges each having an inner edge located adjacent the apex, and an outer edge spaced away from the apex in a medial-lateral direction and extending in a posterior direction from the inner edge toward the outer edge such that the flanges make an angle with one another so as to be placed beneath the bearing surface portions for reinforcing the bearing portion against the load imposed by the condylar elements of the femoral component during service.

The invention will be understood more fully, while still further objects and advantages will become apparent, in the following detailed description of a preferred embodiment of the invention illustrated in the accompanying drawing, in which:

FIG. 3 is a front elevational view of the tibial component;

FIG. 4 is a rear elevational view of the tibial component;

FIG. 5 is a side elevational view of the tibial component;

FIG. 6 is a bottom plan view of the tibial component;

Figure 1:
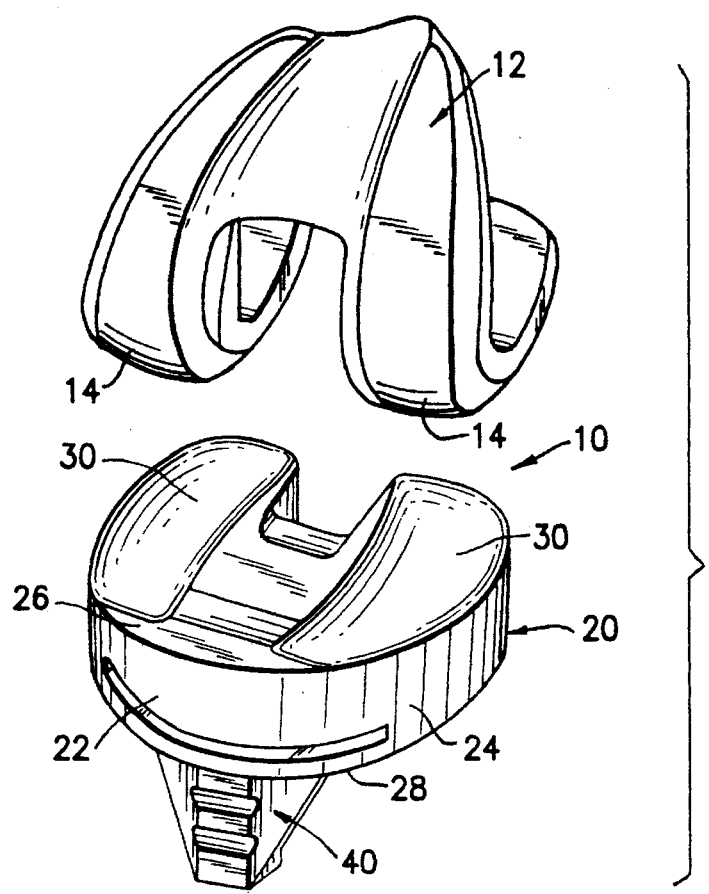
FIG. 1 is an exploded perspective view of a prosthetic knee implant employing a tibial component constructed in accordance with the present invention.
Figure 2:
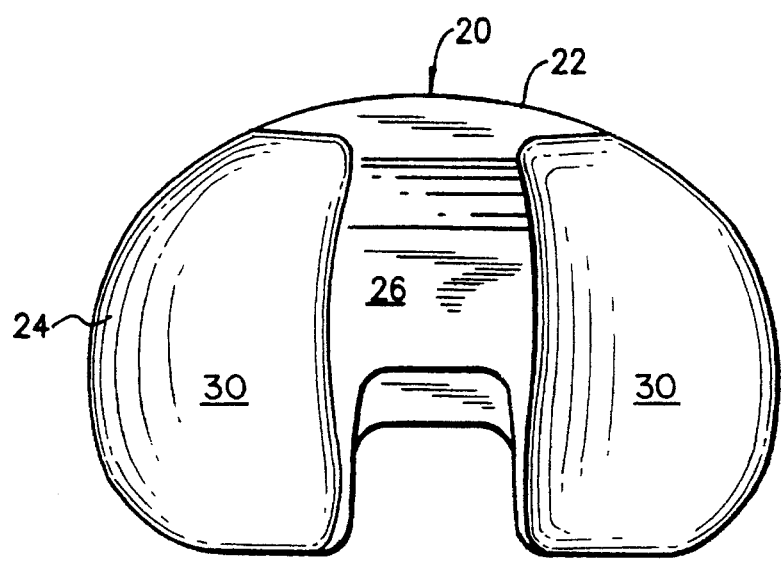
FIG. 2 is a top plan view of the tibial component.
Figure 7:
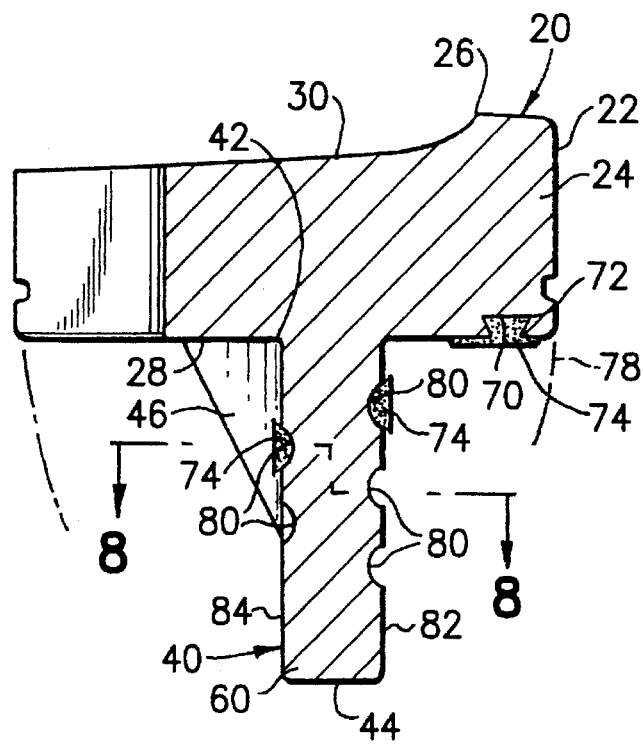
FIG. 7 is an axial cross-sectional view taken along line 7—7 of FIG. 6.

Referring now to the drawing, and especially to FIG. 1 thereof, a prosthetic knee implant illustrated in the form of knee prosthesis 10 includes a femoral component 12 having a pair of laterally spaced apart condylar elements 14. The femoral component is constructed for affixation in the natural femur in a well-known manner. A tibial component for use in the knee prosthesis 10 is shown in the form of tibial component 20 constructed in accordance with the invention and is seen to include a unitary one-piece member 22 of a synthetic polymeric material having a bearing portion 24 with an upper surface 26 and a lower surface 28. Upper surface 26 includes condylar bearing surface portions 30 for engaging and supporting the condylar elements 14 of the femoral component 12 to accept the load imposed by the condylar elements 14 of the femoral component 12 when the tibial component 20 is in service, implanted in the proximal tibia.

Figure 8:
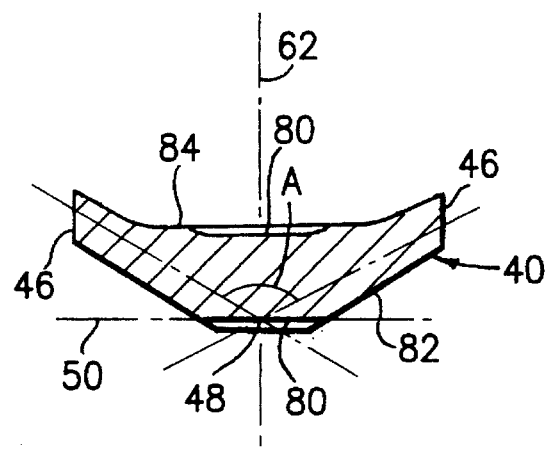
FIG. 8 is a transverse cross-sectional view taken along line 8—8 of FIG. 7.

Turning now to FIGS. 2 through 8, as well as to FIG. 1, tibial component 20 includes a keel 40 projecting in an axial direction downwardly from a proximal end 42 at the lower surface 28 of the bearing portion 24 to a distal end 44 spaced away from the lower surface 28. The keel 40 has a pair of flanges 46 extending in the axial direction and establishing a generally V-shaped overall cross-sectional configuration in planes transverse to the axial direction, as illustrated in FIGS. 6 and 8, the V-shaped cross-sectional configuration having an apex 48 located essentially centrally of the bearing portion 24 along the medial-lateral direction, indicated at 50. The flanges 46 each have an inner edge 52 located adjacent the apex 48, and an outer edge 54 spaced away from the apex 48 in the medial-lateral direction 50. Keel 40 includes a post 60 extending axially along the apex 48 and each flange 46 extends in a somewhat posterior direction from the inner edge 52, located at the post 60, toward the outer edge 54 such that the flanges are swept in the posterior direction at an angle A with one another, the anterior-posterior direction being indicated at 62 in FIGS. 6 and 8.

The angle A is chosen so as to place the flanges 46 beneath the bearing surface portions 30 for reinforcing the bearing portion 24 against the load imposed by the condylar elements 14 of the femoral component 12 during service. At the same time, the angle A directs the flanges 46 into the relatively denser portions of the trabecular bone of the proximal tibia when the tibial component 20 is seated at the implant site so as to enhance the affixation of the tibial component 20 in the proximal tibia. An angle A of about one-hundred-twenty degrees has been found effective to place the flanges 46 of the keel 40 appropriately beneath the bearing surface portions 30 and within the proximal tibia to gain the advantage of gusseting the bearing portion 24 against the loads imposed by the condylar elements 14 of the femoral component 12 and seating the flanges 46 in the denser bone over the range of sizes of the tibial component 20 made available for accommodating recipients of the knee prosthesis 10.

Flanges 46 are tapered axially such that the outer edges 54 extend generally from the post 60 at apex 48 adjacent the distal end 44 of the keel 40 laterally outwardly to the lower surface 28 of the bearing portion 24 adjacent the proximal end 42 of the keel 40. Thus, the orientation of the flanges 46 places the flanges 46 beneath the area of highest load during service and, in concert with the tapered configuration of the flanges 46, enables the flanges 46 to serve as gussets which reinforce the bearing portion 24 and, at the same time, reinforce the post 60 for added stability, thereby enabling the use of a synthetic polymeric material in the construction of the unitary member 22 of the tibial component 20. The tapered configuration of the flanges 46, combined with the angle A, enables relatively deeper and wider penetration of the keel 40 into the proximal tibia for enhanced affixation and stability. Further, angle A provides a symmetrical configuration which enables the same tibial component 20 to be used in connection with either a right or a left knee prosthesis, thereby eliminating the necessity for separate right and left tibial components. The preferred synthetic polymeric material is a high-density polyethylene such as that currently in use as bearing materials in knee prostheses.

Tibial component 20 is affixed in the proximal tibia with cement. In order to enhance the affixation, tibial component 20 includes supplemental affixation means. Thus, a groove 70 extends along the lower surface 28 of the bearing portion 24 and has a keying cross-sectional configuration in axial planes, illustrated in FIG. 7 in the form of a dovetail-shaped cross-sectional configuration 72 within which cement will be interengaged in an interlocking engagement, as seen at 74, to resist axial movement of the bearing portion 24, and tibial component 20, relative to the proximal tibia 78. In addition, as best seen in FIGS. 3 through 8, lateral slots 80 are provided in the keel 40 and extend in the medial-lateral direction 50 for engaging cement 74 in an interlocking engagement to add resistance to axial movement of the keel 40, and tibial component 20, relative to the proximal tibia 78. In the preferred embodiment illustrated herein, three slots 80 are located along the anterior surface 82 of the keel 40 and two slots 80 are located along the posterior surface 84 of the keel 40, with the slots 80 along the anterior surface 82 being staggered axially relative to the slots 80 along the posterior surface 84.

It will be seen that the tibial component 20 of the present invention provides a structural configuration which attains the strength necessary to enable the tibial component to be executed in a unitary construction of a synthetic polymeric material, thus providing a relatively less expensive viable alternate to more complex and costly metallic tibial components, for recipients who do not require the levels of performance and longevity offered by the metallic tibial components. As such, the tibial component attains the several objects and advantages outlined above; namely: Enables the construction of a tibial component in a unitary structure of a synthetic polymeric material, which tibial component provides adequate performance for certain recipients at reduced expense; provides a relatively inexpensive alternative to more costly tibial components constructed of metallic parts where it is indicated that the performance characteristics of the synthetic polymeric tibial component are adequate for a particular recipient; provides a unitary synthetic polymeric tibial component having a structural configuration which reinforces the tibial component against loads imposed during use so as to enable satisfactory performance over an adequate service life; employs a structural configuration which enables increased stability for exemplary performance over a wide variety of conditions encountered during service; facilitates the implant of a knee prosthesis employing the tibial component; enables the economical manufacture of a unitary synthetic polymeric tibial component in practical numbers of uniformly high quality.

It is to be understood that the above detailed description of a preferred embodiment of the invention is provided by way of example only. Various details of design and construction may be modified without departing from the true spirit and scope of the invention, as set forth in the appended claims.

The embodiments of the invention in which an exclusive property or privilege is claimed are defined as follows:

1. A tibial component constructed of a unitary member of synthetic polymeric material for use in a prosthetic knee implant including a femoral component having condylar elements, the tibial component including a bearing portion having an upper surface for confronting the femoral component and a lower surface for engaging the proximal tibia, the tibial component comprising:

condylar bearing surface portions along the upper surface of the bearing portion for engaging the condylar elements of the femoral component and accepting the load imposed by the condylar elements of the femoral component during service; and a keel projecting in an axial direction downwardly from a proximal end at the lower surface of the bearing portion to a distal end spaced away from the lower surface, the keel including a pair of flanges extending in the axial direction and establishing a generally V-shaped overall cross-sectional configuration in planes transverse to the axial direction, the V-shaped cross-sectional configuration having an apex located essentially centrally of the bearing portion along the medial-lateral direction;

the flanges each having an inner edge located adjacent the apex, and an outer edge spaced away from the apex in a medial-lateral direction and extending in a posterior direction from the inner edge toward the outer edge such that the flanges make an angle with one another so as to be placed beneath the bearing surface portions and being tapered axially such that the outer edges extend generally from the lower surface of the bearing portion at the proximal end of the keel to the apex at the distal end of the keel to establish gussets for reinforcing the bearing portion against the load imposed by the condylar elements of the femoral component and stabilizing the keel during service.

2. The invention of claim 1 wherein the synthetic polymeric material is high-density polyethylene.

3. The invention of claim 1 wherein the angle between the flanges is about one-hundred-twenty degrees.

4. The invention of claim 1 wherein the keel includes a post extending axially along the apex of the V-shaped cross-sectional configuration between the proximal end and the distal end of the keel, the flanges being unitary with the post axially along the post for stabilizing the post during service.

5. The invention of claim 1 wherein the tibial component is configured to be affixed to the proximal tibia with cement and the tibial component includes supplemental affixation means for engaging the cement in an interlocking engagement.

6. The invention of claim 5 wherein the supplemental affixation means includes a groove in the lower surface of the bearing portion, the groove having a keying cross-sectional configuration in axial planes for interengaging the cement to resist axial movement of the tibial component relative to the proximal tibia.

7. The invention of claim 5 wherein the supplemental affixation means includes slots in the keel, the slots extending in the medial-lateral direction for interengaging the cement to resist axial movement of the tibial component relative to the proximal tibia.

8. The invention of claim 7 wherein the keel includes an anterior surface and a posterior surface, and the slots extend along at least one of the anterior surface and the posterior surface.

9. The invention of claim 7 wherein the keel includes an anterior surface and a posterior surface, and the slots extend along both the anterior surface and the posterior surface.

10. The invention of claim 7 wherein the keel includes a post extending axially along the apex of the V-shaped cross-sectional configuration and the slots extend across the post in the medial-lateral direction.

11. The invention of claim 10 wherein the keel includes an anterior surface and a posterior surface, and the slots extend along at least one of the anterior surface and the posterior surface.

12. The invention of claim 10 wherein the keel includes an anterior surface and a posterior surface, and the slots extend along both the anterior surface and the posterior surface.

13. The invention of claim 12 wherein the slots along the anterior surface are staggered axially relative to the slots along the posterior surface.

14. The invention of claim 12 wherein the synthetic polymeric material is high-density polyethylene.

* * * * *